United States Patent
Loo et al.

(10) Patent No.: US 12,332,240 B2
(45) Date of Patent: Jun. 17, 2025

(54) COLORIMETRIC SENSING WITH RECONFIGURABLE CHIRAL PLASMONIC STRUCTURES AND A METHOD FOR DETECTING ANALYTES IN SAMPLES USING THE SAME

(71) Applicant: Aalto University Foundation sr, Aalto (FI)

(72) Inventors: Jacky Loo, Espoo (FI); Yike Huang, Espoo (FI); Minh-Kha Nguyen, Espoo (FI); Susanna Hällsten, Espoo (FI); Anton Kuzyk, Espoo (FI); Tim Liedl, Espoo (FI)

(73) Assignee: Aalto University Foundation sr, Aalto (FI)

( * ) Notice: Subject to any disclaimer, the term of this patent is extended or adjusted under 35 U.S.C. 154(b) by 0 days.

(21) Appl. No.: 18/290,827

(22) PCT Filed: Dec. 21, 2022

(86) PCT No.: PCT/FI2022/050859
§ 371 (c)(1),
(2) Date: Jan. 22, 2024

(87) PCT Pub. No.: WO2023/118663
PCT Pub. Date: Jun. 29, 2023

(65) Prior Publication Data
US 2024/0264156 A1    Aug. 8, 2024

(30) Foreign Application Priority Data
Dec. 21, 2021   (FI) ..................... 20217202

(51) Int. Cl.
| C12Q 1/68 | (2018.01) |
| B82Y 15/00 | (2011.01) |
| C12Q 1/6816 | (2018.01) |
| G01N 21/552 | (2014.01) |
| G01N 33/543 | (2006.01) |

(52) U.S. Cl.
CPC ........ *G01N 33/54346* (2013.01); *B82Y 15/00* (2013.01); *C12Q 1/6816* (2013.01); *G01N 21/554* (2013.01); *G01N 33/54386* (2013.01)

(58) Field of Classification Search
CPC .......... G01N 33/54346; G01N 21/554; G01N 33/54386; C12Q 1/6816
See application file for complete search history.

(56) References Cited

PUBLICATIONS

Kuzyk et al: DNA-based self-assembly of chiral plasmonic nanostructures with tailored optical response. Nature, Mar. 15, 2012, vol. 483, pp. 311-314.
Kuzyk et al: Reconfigurable 3D plasmonic metamolecules. Nature Materials, Sep. 2014, vol. 13, No. 9, pp. 862-866.
Lee et al: Amino-acid-and peptide-directed synthesis of chiral plasmonic gold nanoparticles. Nature, Apr. 19, 2018, vol. 556, pp. 360-365.
Liu et al: Freezing Directed Construction of Bio/Nano Interfaces: Reagentless Conjugation, Denser Spherical Nucleic Acids, and Better Nanoflares. J. Am. Chem. Soc., 2017, vol. 139, No. 28, pp. 9471-9474.
Lu et al: Enhanced optical asymmetry in supramolecular chiroplasmonic assemblies with long-range order. Science, Mar. 26, 2021, vol. 371, No. 6536, pp. 1368-1374.
Ma et al: Attomolar DNA detection with chiral nanorod assemblies. Nature Communications, Dec. 1, 2013, vol. 4, No. 1.
Martens et al: Long-and short-ranged chiral interactions in DNA-assembled plasmonic chains. Nature Communications, 2021, vol. 12, No. 2025, pp. 1-6.
Nguyen et al: Chiral assembly of gold-silver core-shell plasmonic nanorods on DNA origami with strong optical activity. ACS NANO, 2020, vol. 14, pp. 7454-7461.
Shen et al: Spiral Patterning of Au Nanoparticles on Au Nanorod Surface to Form Chiral AuNR@AuNP Helical Superstructures Templated by DNA Origami. Advanced Materials, Feb. 20, 2017, vol. 29, No. 1606533, 8 pages.
Xu et al: MicroRNA-Directed Intracellular Self-Assembly of Chiral Nanorod Dimers. Angewandte Chemie, Jul. 3, 2018, vol. 130, No. 33, pp. 10704-10708.

*Primary Examiner* — Jezia Riley
(74) *Attorney, Agent, or Firm* — Laine IP Oy (57) ABSTRACT

The present invention is directed to a nanoscaled construct, said construct comprising or essentially consisting of a nucleic acid structure with reconfigurable or switchable features, and at least two separate metallic nanoparticles coupled with said nucleic acid structure, wherein said two separate nanoparticles are at an interchangeable angle to each other, wherein said nanoparticles provide high chirality and/or optical activity within the visible and near-infrared (NIR) spectrum from 400 to 800 nm generating a color for the construct, and wherein said construct has an absorption dissymmetry factor (g-factor) of over 10%. There is also provided a method for detecting an analyte in a sample, the method comprising steps of contacting a nanoscaled construct of the present disclosure specific to said analyte with a sample in a test assay, and detecting said analyte in said sample by optical means or by naked eye, wherein the presence of the analyte in said sample changes the color of said nanoscaled structure and the change of color in said assay confirms the presence of the analyte in said sample.

22 Claims, 7 Drawing Sheets
Specification includes a Sequence Listing.

COLORIMETRIC SENSING WITH RECONFIGURABLE CHIRAL PLASMONIC STRUCTURES AND A METHOD FOR DETECTING ANALYTES IN SAMPLES USING THE SAME

FIELD

This invention relates to a reconfigurable structure generating a colormetric readout for colorimetric sensing in chemical and biological detection assays.

BACKGROUND

Visual-based sensing has been an increasingly popular field of research since its sensing reaction can take place in a simple test tube without external components and a central laboratory. This merit is desirable and particularly essential for on-site point-of-care tests in remote areas and mobile testing points.

Visual-based sensing includes chemical-based and plasmonic-based colors. Conventional approaches of visual-based chemical-based sensing rely on chemical reactions that result in a change in color absorption or transmission, fluorescence or luminescence. Typical examples include ELISA and PCR, which make use of chemical dyes and chemical fluorescence probes to generate a visual color.

Noble metal nanoparticles (NP) have been widely used for developing colorimetric sensing or detection schemes. In NP solution, the presence of an analyte leads to a significant color and/or intensity change, and this change can often be detected with the naked eye. One conventional approach to visual-based plasmonic-based sensing in solution is NP-mediated sensing, such as quantum dots, which provide a high intensity of the luminescence at a nanoscale spot, significantly improving the fluorescent signal. The use of gold nanosphere (AuNSs) in analyte-induced AuNSs aggregation assays provides a visual absorptive color change, such as the color representation in a line in lateral flow assay. On the other hand, gold nanorods (AuNRs) show a plasmonic color response that depends on polarization. Since the plasmonic coupling of AuNRs exhibits two orthogonal plasmon resonances, the controlled plasmon coupling of NR dimers with a precise spatial configuration can regulate the aggregation orientation to enhance the localized surface plasmon resonance (LSPR) signal for biosensing. In addition, the specific geometry of gold nanorods will induce extrinsic anisotropic property, i.e. chirality.

Reconfigurable chiral plasmonic structures have emerged as a promising candidate for developing novel sensing schemes. These structures' sensing or detection mechanism is based on the strong correlation between the spatial configuration of chiral plasmonic structures and their chiroptical responses. The geometry control in NR dimers allows polarization-dependent plasmon resonances, bringing a quantifiable change in chirality, i.e. circular dichroism (CD) signals. These changes or signals can then be detected by CD spectroscopy. Such chiral plasmonic sensors have several unique advantages: (i) high sensitivity; (ii) strong modulation of optical responses to an analyte; (iii) reliable optical detection in an environment with strong optical extinction.

Operation in biologically relevant conditions is prohibitively complex. Auto-fluorescence naturally occurs in biological samples, causing false-positive signals. Visualization of fluorescence signals requires a more complicated optical setting and a fluorescent excitation path to observe the fluorescent emission color. Besides, traditional chemical dyes or fluorescence come with several shortcomings, e.g. low stability, quenching effect and auto-fluorescence.

An alternative is the use of nanomaterials, but, in analyte-induced aggregation plasmonic sensing, undesirable aggregation can be triggered by impurities in biological samples. Aggregation of NP can be induced or inhibited by environment variations (pH value, temperature, unspecific binding of molecules, etc.) instead of the presence of the analyte. Therefore, it results in high false positive/negative rates of colorimetric sensors.

For the measurement of chirality, i.e. CD signals, the readout schemes heavily rely on CD spectroscopy, which requires expensive and bulky equipment with sophisticated optic design. This has limited the utility of chiral plasmonic sensors outside of the laboratory. In addition, conventional chirality-based sensing approaches with nanomaterials show small modulation of optical responses, i.e. weak intensity and/or limited color change of the solution due to the low chirality, and they are often unsuitable for reliable detection with the naked eye.

The approach of the present inventors relies on the structural reconfiguration of nanoparticle assemblies with nanoscale-precision control, not on the poorly controlled aggregation process. Reconfiguration is a key step for tunable chirality in this current chiral-based sensing systems for analytical functionalities. The effects of environmental variations are minimal compared to the nanoparticle-aggregation based paper strip assay. Our reconfigurable nanostructure has also shown better accuracy than the nanoparticle-aggregation assay. In addition, the modulation of optical responses in our system is strong enough to be determined with the naked eye, and the visual responses can be adjusted to the spectral regions most suitable for naked-eye detection via simple optical settings with polarizers.

SUMMARY OF THE INVENTION

The object of the invention is the development of a chiral plasmonic sensing scheme with a reconfigurable nanoscaled construct of record-high anisotropy factors (g-factors) up to 16%, as well as its tunable chirality reaching a range of anisotropy factor from 0-16%. Such high and dynamic g-factors enable colorimetric detection that can be distinguished by the naked eye. The analyte-dependent modulation of chiroptical responses that change in colorimetric signal supports the optical readout that does not rely on CD spectrometry. The reconfigurable nanoscaled construct could be fabricated with the DNA origami technique, and recognition elements for sensing can be added into the assemblies to detect the presence of a target analyte. The possibility to dynamically control the nanoscaled construct enables visual color change for sensing. The angle of the nanoscaled construct poses a significant effect on the chirality. The angle is controlled by the origami bridge sequence length. Chirality increases when the angle changes from the open configuration, in which two origami bundles are perpendicular or are nearly perpendicular to each other, e.g. 90°, to the closed configuration, e.g. 45°.

Dynamic feature in response to analyte binding in biosensing can be obtained in the reconfigurable plasmonic assemblies, i.e. the nanoscaled construct, to act as chiral plasmonic switches that exhibit dynamic response, i.e. switching between open and close configuration, which results in a significant change in chirality, hence the change in colorimetric readout signal in terms of color and intensity. The colorimetric detection expands the utility of chiral plasmonic sensors beyond laboratory settings and makes them suitable for diagnostics and sensing applications in the point-of-care and/or remote-area scenarios.

In our approach, the plasmonic color within the visible wavelength spectrum with a tunable range structural reconfiguration and selection of metallic nanomaterials or nanoparticles provides a versatile choice of color. When the recognition element is attached, the reconfigurable or switchable feature, which tunes the chirality, shows the responsivity feature in sensing, biosensing and analytical applications. Colorimetric chiral-based sensing shows significant advantages over existing colorimetric sensing approaches:

A) Minimal effects of environmental variations.
B) Reduced rates of false-positive and negative results.
C) Straightforward modification of biorecognition elements for a wide range of targets.
D) The ability to operate in physiologically relevant environments.
E) Intense modulation of optical responses that can be observed with the naked eye.
F) Fast detection or sensing capabilities with a conventional readout since there is no need for sample purification or signal amplification
G) Ability to perform reliable sensing or detection outside of the laboratory.

The invention is defined by the features of the independent claims. Some specific embodiments are defined in the dependent claims.

According to a first aspect of the present invention, there is provided a nanoscaled construct, said construct comprising or essentially consisting of a nucleic acid structure with reconfigurable or switchable features, and at least two separate metallic nanoparticles coupled with said nucleic acid structure, wherein said two separate nanoparticles are at an interchangeable angle to each other, wherein said nanoparticles provide high chirality and/or optical activity within the visible and near-infrared (NIR) spectrum from 400 to 800 nm generating a color for the construct, and wherein said construct has an absorption dissymmetry factor (g-factor) of over 10%.

According to a second aspect of the present invention, there is provided a method for detecting an analyte in a sample, the method comprising steps of contacting a nanoscaled construct of the present disclosure specific to said analyte with a sample in a test assay, and detecting said analyte in said sample by optical means or by naked eye, wherein the presence of the analyte in said sample changes the color of said nanoscaled structure and the change of color in said assay confirms the presence of the analyte in said sample.

According to a third aspect of the present invention, there is provided a use of a nanoscaled construct of the present disclosure for the detection of an analyte in a sample, wherein the presence of the analyte in said sample changes the color of said nanoscaled structure when contacted with said sample and the change of color confirms the presence of the analyte in said sample.

EMBODIMENTS

In the present context, the expression "functionalization", as used herein, means the occurrence of oligonucleotide or DNA on the metallic nanoparticles.

The calculation of the g-factor in percentage (%) is by the CD value (millidegree) divided by the absorbance at their wavelength, and further divided by 32980 and multiplied by 100.

The expression "g-factor" in percentage (%), as used herein, means the net value or magnitude of the g-factor, which can be a positive or negative value. In the present disclosure, we utilized DNA origami techniques for the fabrication of a reconfigurable nanoscaled construct with record-high anisotropy factors (g-factors), which is defined as $$g = 2\frac{((A_L - A_R)}{(A_R + A_L))},$$

where $A_L$ and $A_R$ are absorptions for the left- and right-handed circularly polarized light, respectively, up to 16%, as well as its tunable chirality to reach a range of anisotropy factor from 0-16%. Such high g-factors enabled colorimetric detection (simple detection by the naked eye) of analyte-dependent modulation of chiroptical responses. Therefore, the developed chiral plasmonic sensing scheme with an optical readout does not require CD spectrometry.

Some embodiments and examples of the invention are described in the following.

For the construction of a characterization platform according to embodiments of the invention, the following materials can be used: Scaffold DNA strands, staple strands including core and bridge strands, testing strands (NAL and its complementary strands), metal nanoparticles, thiol-modified DNA strands, nuclease-free water, buffers, analyte chemicals, sodium chloride, magnesium chloride, surfactants (e.g., sodium dodecyl sulfate (SDS), Tween 20).

In embodiments of the invention, for the use of the platform, the following equipment can be used: thermocycler, thermoshaker, centrifuge, and polarizers. For details, see the Examples below.

Figure 1A:
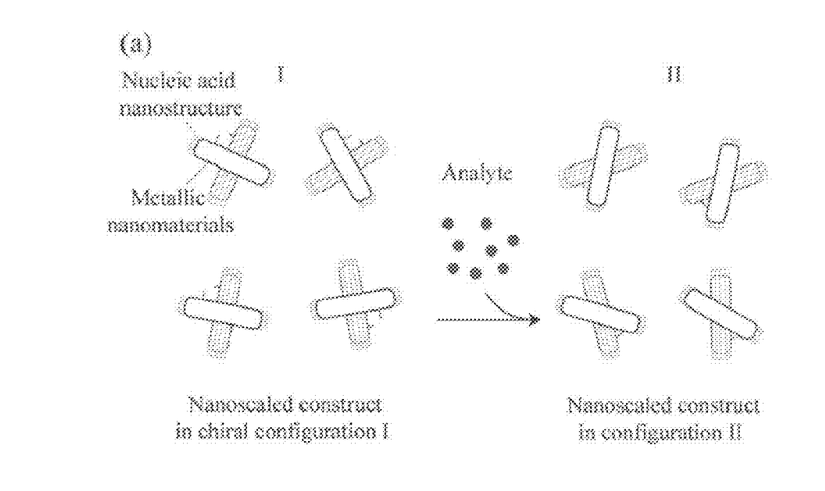
FIG. 1 is the schematic diagram illustrating (a) the reconfigurable feature of our nanoscaled construct during sample detection, and (b) the colorimetric detection scheme with our nanoscaled construct.
Figure 1B:
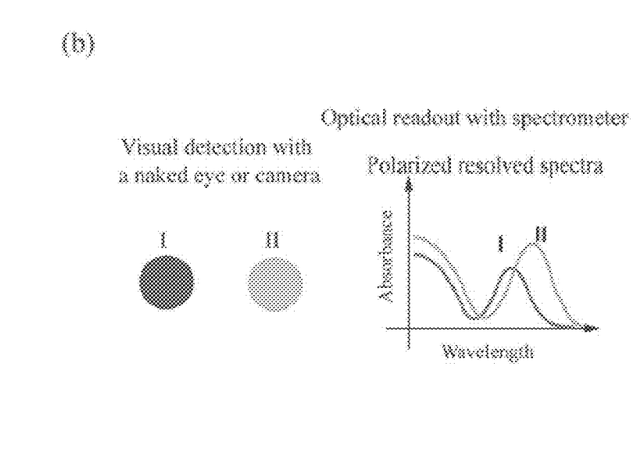

An embodiment of the invention is composed of Reconfigurable Chiral Plasmonic Structures that enables Colorimetric Sensing method for detecting samples of certain chirality. FIG. 1 is the overview of Colorimetric chiral-based sensing schemes, showing an exemplary embodiment of the nanoscaled construct and its detection scheme. In this embodiment, the nanoscaled construct, showing chiral colorimetric sensing by analyte-induced modulation of chiroptical responses in this invention, enables a readout that does not depend on CD spectroscopy. The measurement method is a visual observation by the eyes, digital camera or spectrometer.

Figure 2:
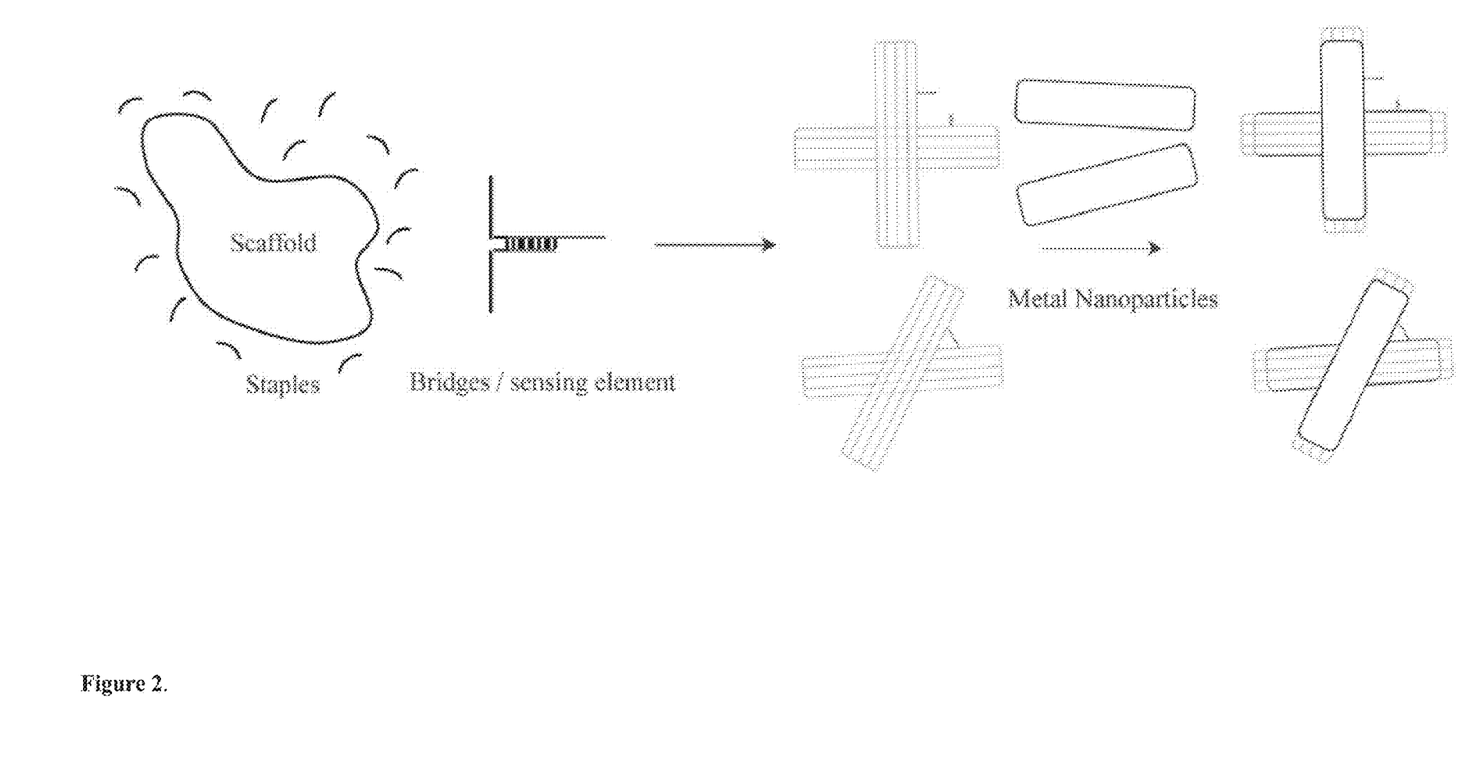
FIG. 2 is a schematic diagram illustrating the construction of the nanoscaled construct.

FIG. 2 shows a schematic diagram illustrating the construction of the nanoscaled construct. The nanoscaled constructs are composed of DNA origami and metal nanoparticles. The bridges or sensing elements are inserted during the DNA origami assembly through an annealing process. The metal nanoparticles are assembled on the DNA origami to build the nanoscaled construct. The use of nanorods can provide a wide colorimetric range on the visual spectrum. It can also provide relatively simple optical observation and distinguishment compared to previous chiral visual sensing. The benefits of the invention are (i) the fabrication process requires fewer steps; and (ii) high efficiency of insertion of the bridges or sensing elements into the nanoscaled construct.

Figure 3A:
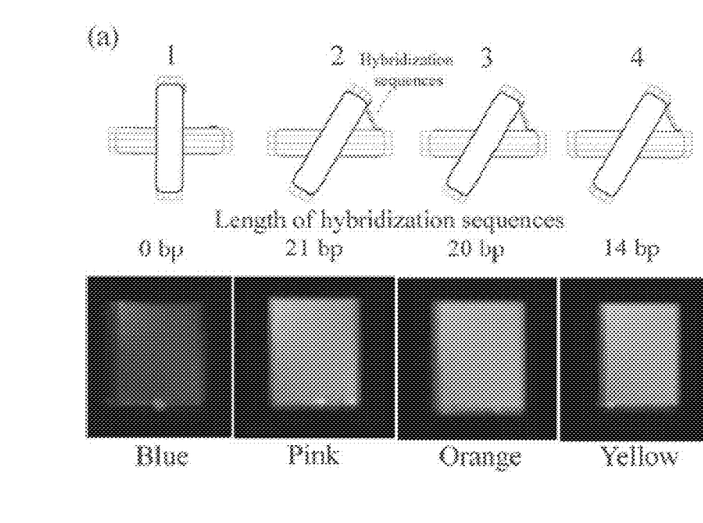
FIG. 3 is a schematic diagram (a) illustrating the tunable angle features with defined lengths of bridge strands to the resulted chiral signal in terms of the corresponding color images, (b) the spectrum of anisotropy factors with wavelength, and (c) polarization-resolved spectrometric graph.
Figure 3B:
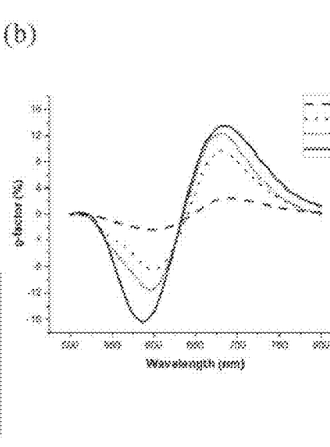
Figure 3C:
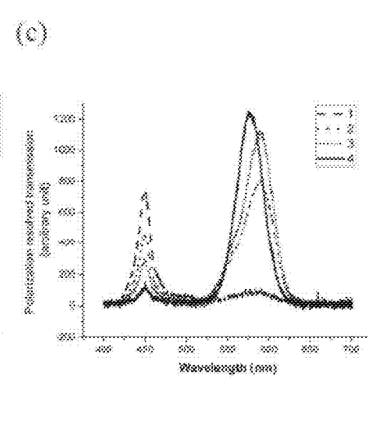

In our solution, fixed bridge strands of defined sequences were used for defined angles to reach defined chirality. FIG. 3 shows an example of the reconfigurable angle feature (i.e. interchangeable angles) in chirality, and a spectrum of anisotropy factors with wavelength and color images. Different configurations with DNA origami linked with different bridges correspond to their signals. The configurations comprise various bridges of defined lengths to join two DNA bundles to adjust their angular rotation to particular angles, which result in different chirality and hence observable color difference.

Figure 4A:
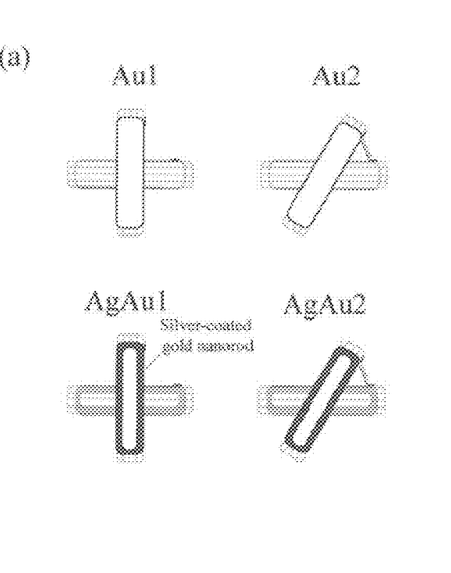
FIG. 4 shows (a) a schematic diagram of the illustration, (b) a spectrum of anisotropy factors with wavelength, and (c) color images of tunable colorimetric signals of the nanoscaled construct of the same open and close configuration with the use of different composition nanomaterials AuNR (Au1 and Au2) and Au@AgNR (AgAu1 and AgAu2).

Metal particles are anchored on the DNA origami and generate an optical signal due to the plasmonic coupling effect. FIG. 4 shows an example of the tunable visual color with the use of different composition nanomaterials, e.g. AuNRs and Au@AgNRs, in the nanoscaled construct of similar chirality. The nanoscaled construct may be configured to join with different plasmonic nanomaterials of a varying absorption spectrum. It leads to the change in CD spectrum as well as the colorimetric readout in terms of color and intensity.

Nanoscaled constructs, wherein different metallic nanomaterials are different in size, shape, and composition, can be used in the present invention. Metallic nanomaterials that are used in nanoscaled construct can be gold nanorods, or silver-coated gold nanorods.

The size of the gold or silver-coated nanorods that generate tunable g-factors can range from length between 60 and 90 nm, preferably between 65 and 80 nm, and diameter between 20 and 50 nm, preferably 25 and 40 nm. A preferred mean size is about 70 nm in length and 30 nm in diameter. In general, the nanoscaled construct with nanorods increase in size will increase the g-factors in both open and close configurations. For example, the g-factor with nanoscaled construct with gold nanorods of size ~70 nm in length and ~30 nm in diameter is higher than that of size ~65 nm in length and ~25 nm in diameter. Preferably, the use of nanorods that increase in uniformity increases the nanoscale construct g-factor>10%.

Gold nanorods of different shapes can be used in the nanoscaled construct to produce different colors of the similar g-factor. For example, gold nanorods with round edges produce different colors than gold nanorods with sharp edges.

Figure 4B:
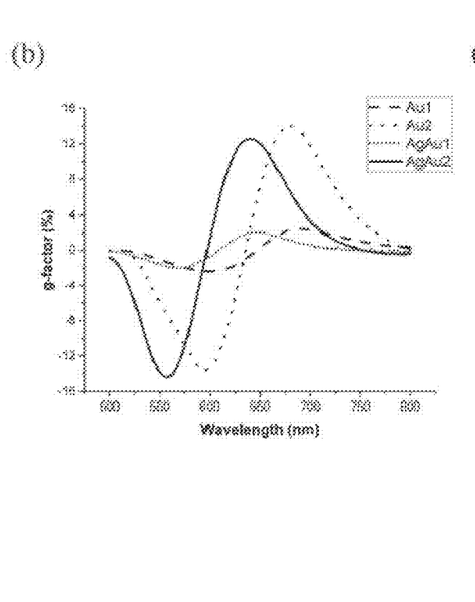
Figure 4C:
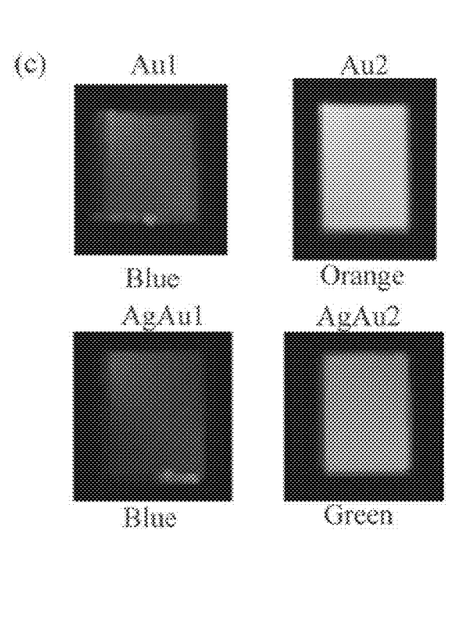

Different metallic nanomaterials, in terms of size of the silver thickness coating, for example, 5 nm silver coating, AuNR that can generate different optical responses which shift optical response and g-factor in the visual and near-infrared (NIR) spectrum (FIG. 4). Both AuNR (in the example of Au2) and Au@AgNR (in this example of AgAu2) used in the nanoscaled construct of close configuration give the g-factor ~15%, while g-factor peaks using Au2 are in the range between 575-625 nm and 650-700 nm, and g-factor peaks using Au2 are in the range between 550-580 nm and 620-660 nm (FIG. 4b). The optical responses are different. For example, the color of Au2 is orange while AgAu2 is green (FIG. 4c).

Different metallic nanomaterials, in terms of size of the silver thickness coating (from without=0 nm to 8 nm coated) AuNR can generate different optical responses which shift optical response and g-factor range from 400-800 nm.

Without silver thickness coating of the AuNR, the nanoscaled construct g-factor peaks are in the range between 575-625 nm and 650-700 nm.

From the range of above 0 nm and below 3 nm silver thickness coating of the AuNR, the nanoscaled construct g-factor peaks are in the range between 580-620 nm and 650-690 nm.

From the range of above 3 nm and below 6 nm silver thickness coating of the AuNR, the nanoscaled construct g-factor peaks are in the range between 560-600 nm and 620-660 nm.

From the range of above 6 nm and below 9 nm silver thickness coating of the AuNR, the nanoscaled construct g-factor peaks are in the range between 530-570 nm and 590-630 nm.

The tunable color generation, which is detectable by the optical sensor with spectrometer, in term of change in intensities of wavelengths, or shift in wavelength maximum. In the above examples, the g-factor peaks are 4 to 6% in close configuration, while the color can be different.

In an embodiment, the color of nanoscaled construct of close configuration with AuNR shows pink color. In another embodiment, the color of nanoscaled construct of close configuration with above 0 nm and below 3 nm silver thickness coating of the AuNR shows purple-cyan color. In another embodiment, the color of nanoscaled construct of close configuration with above 3 nm and below 6 nm silver thickness coating of the AuNR show bluish green color. In another embodiment, the color of nanoscaled construct of close configuration with above 6 nm and below 9 nm silver thickness coating of the AuNR show green color.

Figure 5A:
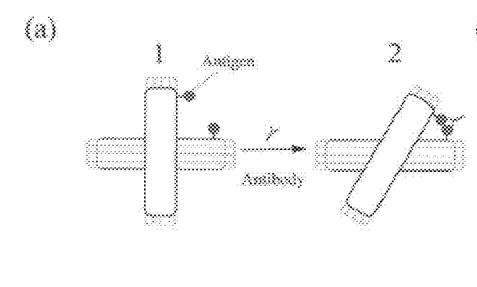
FIG. 5 shows (a) a schematic diagram of the illustration, (b) a spectrum of anisotropy factors with wavelength, and (c) color images of examples of analyte dependent configuration modulation of chiral plasmonic assemblies for protein sensing.
Figure 5B:
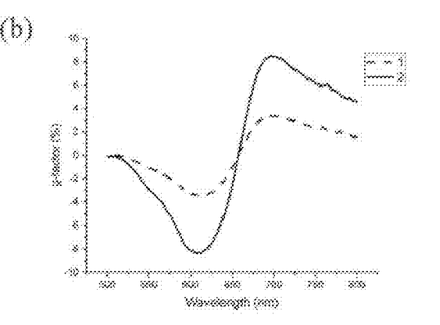
Figure 5C:
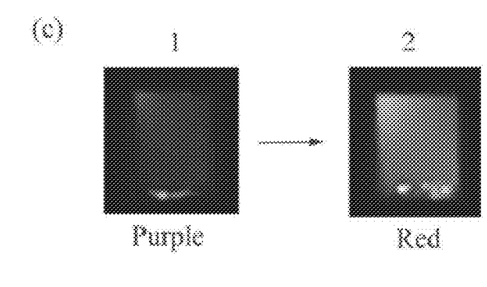
Figure 6A:
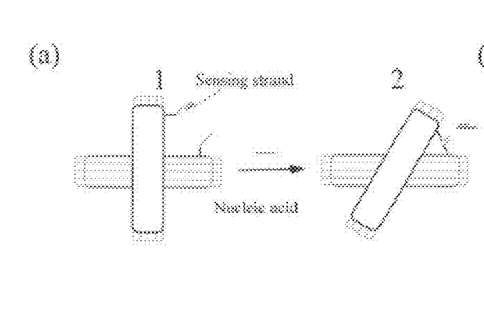
FIG. 6 shows (a) a schematic diagram of the illustration, (b) a spectrum of anisotropy factors with wavelength, and (c) color images of examples of analyte dependent configuration modulation of chiral plasmonic assemblies for nucleic acid sensing.
Figure 6B:
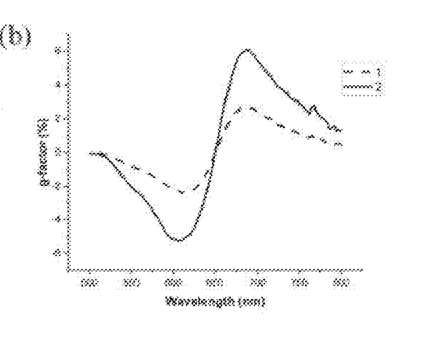
Figure 6C:
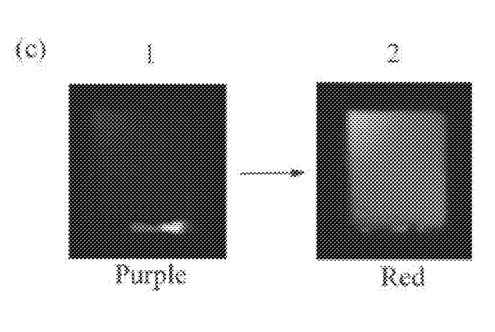
Figure 7A:
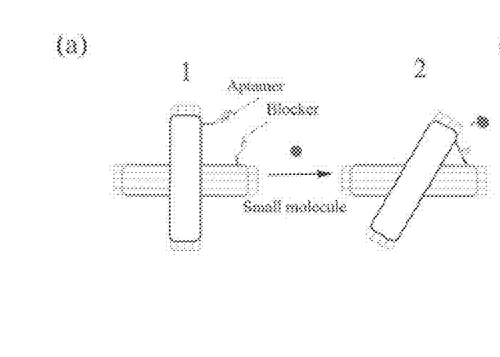
FIG. 7 shows (a) a schematic diagram of the illustration, (b) a spectrum of anisotropy factors with wavelength, and (c) color images of examples of analyte dependent configuration modulation of chiral plasmonic assemblies for small molecule sensing.
Figure 7B:
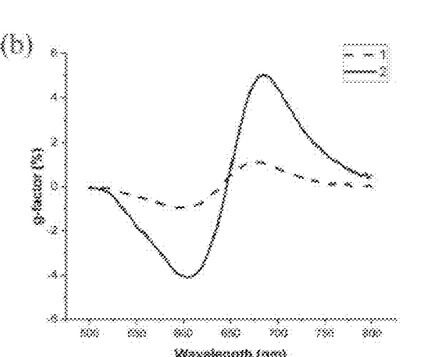
Figure 7C:
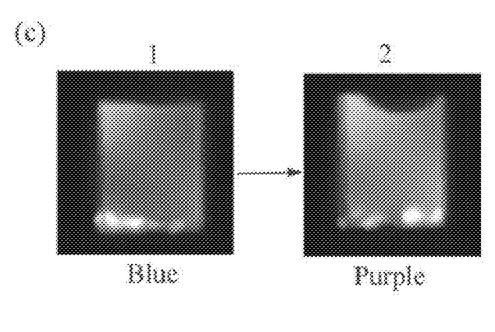

The sensing reaction is based on the change in the chirality of the present structure. Visual readout by the dynamic chiral response for sensing is illustrated in FIG. 5-7. The sensing relies on analyte dependent configuration modulation of chiral plasmonic assemblies for protein, nucleic acid and small molecules sensing, respectively. Analyte interaction leads to strong modulation of plasmonic optical responses for visual absorptive or transmission color from one specific color to another. As shown in FIGS. 5 to 7, upon the presence of the analyte, the chirality in terms of CD signals has increased, and the colorimetric signal changes from one color to another.

Similar to the sensing of nucleic acids, the sensing of small molecules, e.g. adenosine triphosphate (ATP), is based on the dissociation of a strand, i.e. an aptamer strand targeting the small molecules is dissociated in the presence of the ATP. This leads to hybridization of two bridge sequences in the origami, thus changing the angle of the nanoscaled construct.

Spatially reconfigurable chiral plasmonic structures have emerged as a promising candidate for the development of novel sensing schemes. Here, the sensing or detection mechanism is based on the strong correlation between the spatial configuration of chiral plasmonic structures and their chiroptical responses. Chiral plasmonic sensors have several unique advantages: (i) high sensitivity; (ii) strong modulation of optical responses in response to an analyte; (iii) reliable optical detection in environments with strong optical extinction. Chiral plasmonic sensors rely on analyte dependent configuration modulation of chiral plasmonic assemblies in the nanoscaled construct. So far, the readout has relied on CD spectroscopy. This invention enables a readout that does not rely on CD spectroscopy, e.g. the analyte induced modulation of chiroptical responses can be observed with the naked eye. Such high g-factors enabled colorimetric detection (simply distinguished by a naked eye) of analyte-dependent modulation of chiroptical responses. Colorimetric detection greatly expands the utility of chiral plasmonic sensors beyond laboratory settings and makes them suitable for diagnostics and sensing applications in the point-of-care and/or remote-area scenarios.

The switching of this nanoscaled construct from open to closed and vice versa for visual detection makes it a nanoscaled construct to be utilized in a wide range of applications in the chiral sensing field, e.g. chiral plasmonic sensing in biomedical applications. Examples 3-5 below are the visual detection with an open-to-close feature of the nanoscaled construct, the open-to-close feature of which can be changed by direct binding of a target analyte or dissociation of the component, e.g. sensing strand, from the nanoscaled construct in the presence of the target analyte.

The embodiments and the methods of the present invention may be implemented using certain hardware, software, or a combination thereof for colorimetric observation and analysis. In an embodiment, a developing kit can be prepared, the kit containing the materials that fabricate the present nanoscaled construct, where the users can add their desired recognition element and bridge sequences, e.g. short nucleic acid sequences, that hybridize with the present structure and to perform sensing with the target analyte. The users could opt to optimize the bridge sequence until the desired color change can be observed.

In an embodiment, a detection kit may contain the nanoscaled construct of the present disclosure in a cartridge or plastic strip to hold the sensing solution premix and enable sample injection. The sensing solution premix comprising the present nanoscaled construct with the recognition element, e.g. SARS-CoV2 antibody, can target a specific analyte, in this case a SARS-CoV2 antigen. In this method, the user will just need to add the sample, e.g. saliva, of a defined volume assisted by a dropper to the cartridge or plastic strip and observe the color change, e.g. from blue to red, with the naked eye, or place the cartridge or plastic strip into the optical reader for readout, or record by a camera.

Further embodiments of the present disclosure are:
1. A nanoscaled construct essentially consisting of nucleic acid structures with reconfigurable or switchable features, and metallic nanomaterials, wherein high chirality and/or optical activity, defined as having an absorption dissymmetry factor (g-factor) over 10%, is obtained.
2. The nanoscaled construct of embodiment 1 includes ensemble of nucleic acid structures and metallic nanomaterials.
3. The nanoscaled construct of embodiment 1, wherein the chirality and/or optical activity range lies within the visible and near-infrared (NIR) spectrum from 400 to 800 nm.
4. The nanoscaled construct of embodiment 3, wherein the chirality and/or optical activity range is tunable or adjustable within the visible and NIR wavelength spectrum from 400 to 800 nm.
5. The nanoscaled construct of embodiment 1, wherein the chirality and/or optical activity is tunable or adjustable.
6. The nanoscaled construct of embodiment 5, wherein the chirality and/or optical activity is reversibly tunable or adjustable by the reconfigurable or switchable action.
7. The nanoscaled construct of embodiment 6, wherein the reconfigurable or switchable feature is reversible.
8. The nanoscaled construct of embodiment 6, wherein the chirality and/or optical activity is tunable or adjustable by geometry and/or angle change of the nanoscaled construct.
9. The nanoscaled construct of embodiment 6, wherein the chirality and/or optical activity is tunable or adjustable by using different metallic nanomaterials.
10. The nanoscaled construct of embodiment 9, wherein different metallic nanomaterials are different in size, shape and composition.
11. The nanoscaled construct of embodiment 1, wherein the metallic nanomaterials are metallic nanoparticles.
12. The nanoscaled construct of embodiment 11, wherein the metallic nanoparticles are metallic nanorods.
13. The nanoscaled construct of embodiment 11, wherein the metallic nanomaterials are gold nanorods or nanorods composed of gold and silver.
14. The nanoscaled construct of embodiment 6, wherein the chirality and/or optical activity is tunable or adjustable by the combined effect of geometry and/or angle change of the nanoscaled construct and the use of different metallic nanomaterials.
15. The nanoscaled construct of embodiment 1, wherein the color generation is based on the chirality and/or optical activity.
16. The nanoscaled construct of embodiment 15, wherein the color generation is based on the chiral optical response from metallic nanomaterials.
17. The nanoscaled construct of embodiment 4, wherein the tunable color generation is based on the tunable chirality and/or optical activity.
18. The nanoscaled construct of embodiment 15, wherein the said color generation is optically detectable by eye and/or optical sensor.
19. The nanoscaled construct of embodiment 17, wherein the said tunable color generation is optically detectable by the eye and/or an optical sensor.
20. The nanoscaled construct of embodiment 15, wherein the color is optically detectable with the aid of polarizer or polarizers.
21. The nanoscaled construct of embodiment 15, wherein the color of the spectral feature can be quantitatively measured by an optical sensor.

22. The nanoscaled construct of embodiment 1, wherein said responsivity to external stimuli is enabled.
23. The nanoscaled construct of embodiment 22, wherein the responsivity is equivalent to the change in chirality and/or optical activity, or change in g-factor from 0 to over 10%.
24. The nanoscaled construct of embodiment 22, wherein the external stimulus is the target analyte.
25. The nanoscaled construct of embodiment 22, wherein said nanoscaled construct contains a peptide or oligonucleotide as the bioreceptor, sensing or recognition element.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment", "an embodiment", or "preferred embodiment" means that a particular feature, structure, or characteristic described in connection with the embodiment is included in at least one embodiment of the present invention. Thus, appearances of the phrases "in one embodiment", "in an embodiment", "in a preferred embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", i.e. a singular form, throughout this document does not exclude a plurality.

EXAMPLES

Materials used in the example cases below for the construction of nanostructured molecule: DNA scaffold strands (p7650) purchased from tilibit nanosystems GmbH, Germany; Staple strands from ThermoFisher; other DNA/RNA strands from IDT; Thiol-modified TTTTT TTTTT TTTTT T (SEQ ID NO:20) DNA strands from Biomers. Bridge and sensing strands are listed in Table 1.

TABLE 1

Sequences of bridge and sensing strands

| Name | Sequence |
|---|---|
| Design1-seq1 | ATACCAAATCGCCTATGTTACCTTTGAATCAAGAG AAATCAATCTCCGCCACTACACTCAACTC (SEQ ID NO: 1) |
| Design1-seq2-21nt | TGAGAGTTCGTAAAACAGGAAGCATTAAT GAGTTGAGTGTAGTGGCGGAG (SEQ ID NO: 2) |
| Design2-seq1 | ATACCAAATCGCCTATGTTACCTTTGAATCAAGAG AAATCAATCTCCGCCACTACACTCAACTCAAATAC (SEQ ID NO: 3) |
| Design2-seq2-20nt | GATGTTGCTTGGTAAT AGTTGAGTGTAGTGGCGGAG (SEQ ID NO: 4) |
| Design2-seq2-14nt | GATGTTGCTTGGTAAT GTGTAGTGGCGGAG (SEQ ID NO: 5) |
| Design2-seq3 | TGAGAGTTCGTAAAACAGGAAGCATTAATTTACCA AGCAACATC (SEQ ID NO: 6) |
| Design2-seq4 | CGTAACAAAGCTGGCTGGCTGACCTTCAAGAGGAC (SEQ ID NO: 7) |
| AbsSense-seq1 | ATACCAAATCGCCTATGTTACCTTTGAATCAAGAG AAATCAATTT/3Dig_N/ (SEQ ID NO: 8) |
| AbsSense-seq2 | TGAGAGTTCGTAAAACAGGAAGCATTAATTT/ 3Dig_N/ (SEQ ID NO: 9) |
| NASense-seq1 | ATTGCCCAAGACTTGTGTGTTGAGTTGAGTGTAGT GGCGGAG (SEQ ID NO: 10) |
| NASense-seq2 | TGAGAGTTCGTAAAACAGGAAGCATTAATTCACAC AAGTCTTG (SEQ ID NO: 11) |
| NASense-sensing strand | CACACAAGTCTTGGGCAATTTGCTTCAATGC (SEQ ID NO: 12) |
| NA | GCATTGAAGCAAATTGCCCAAGACT (SEQ ID NO: 13) |
| SMSense-seq1 | ATACCAAATCGCCTATGTTACCTTTGAATCAAGAG AAATCAATGAACCTCACTACAGTCAACTC (SEQ ID NO: 14) |

TABLE 1-continued

Sequences of bridge and sensing strands

| Name | Sequence |
|---|---|
| SMSense-seq2 | TCCCCCAGGTCGCGTGAGTTGACTGTAGTGAGGTTC (SEQ ID NO: 15) |
| SMSense-seq3 | TGAGAGTTCGTAAAACAGGAAGCATTAATTCGCGACCTGGGGGAGTATTGCGGAGGAAGGT (SEQ ID NO: 16) |
| SMSense-blocker | GCTTCAATGCCACTTGTGTCCCCCAGGT (SEQ ID NO: 17) |
| SMSense-aptamer | CGCGACCTGGGGGAGTATTGCGGAGGAAGGT (SEQ ID NO: 18) |
| SMSense-activate | GGGGGACACAAGTGGCATTGAAGC (SEQ ID NO: 19) |

Designs 1-2 are comprised of different bridge designs of different hybridization geometries, sequences and lengths that can adjust the angle and geometry between two bundles of the origami structure in our nanoscaled construct. In the examples of embodiment of our nanoscaled construct made for various sensing applications, bridges of from AbsSense (AbsSense-seq1, AbsSense-seq2) for protein sensing, NASense (NASense-seq1, NASense-seq2, NASense-sensing strand) for nucleic acid sensing of target sequence (NA), SMSense (SMSense-seq1, SMSense-seq2, SMSense-seq3, SMSense-blocker, SMSense-aptamer, SMSense-activate) for small molecules sensing are used.

As an example for the construction of origami of the nanoscaled construct in an embodiment:

To prepare staple solutions, 156 core strands, bridge strands with or without the sensing element are mixed at the ratio of 1:1.5. Ten microliter of staple (0.64, 0.96, 1.3 µM for core, bridge and sensing strands) solution was mixed with 5 µL TE (10×), 5 µL scaffold p7560 (100 nM), 10 µL MgCl$_2$ (100 mM), 2.5 µL NaCl (100 mM), 17.5 µL H$_2$O. The mixture was annealed from 80° C. to room temperature for approximately 28 hours to synthesize the DNA origami structures. The DNA origami was purified through agarose gel purification. The concentration of DNA origami was calculated by measuring the absorbance at 260 nm (ext. co. 1.3×10$^8$ M$^{-1}$ cm$^{-1}$) with a spectrometer. DNA origami samples were stored at 4° C. in DNA lobind tubes.

As an example for the construction of gold nanorod (AuNR) and defined thickness of the silver coating on AuNRs to obtain silver-coated AuNRs (Au@AgNR) in the nanoscaled construct in an embodiment:

Formation of the gold seed was performed prior to synthesis of small AuNR and growth to the desired size and aspect ratio of AuNR. The gold seed solution was first prepared by mixing 20 µL HAuCl$_4$ (50 mM) and 10 µL L-ascorbic acid (100 mM) with 2 mL of the mixture of 1-decanol (13.5 mM) and hexadecyltrimethylammonium bromide (CTAB, 50 mM) at 25° C. 80 µL NaBH$_4$ (20 mM) was injected quickly into the solution under vigorous stirring. The seed solution was incubated for 1 hour at 25° C. before use. Small AuNR was synthesized by gently mixing 240 µL AgNO$_3$ (10 mM), 300 µL HAuCl$_4$ (50 mM), 390 µL L-ascorbic acid (100 mM), 2.1 mL HCl (1 M), and 1.8 mL gold seed with 30 mL of the mixture of 1-decanol (13.5 mM) and CTAB (50 mM) at 25° C. After incubating for 4 hours at 25° C., Small AuNR was purified and diluted to OD$_{400\ nm}$=10 in 10 mM CTAB. Then, AuNR was prepared by gently mixing 600 µL AgNO$_3$ (10 mM), 200 µL HAuCl$_4$ (50 mM), 160 µL L-ascorbic acid (100 mM), 100 µL HCl (1 M), and 130 µL small AuNR with 20 mL of the mixture of 1-decanol (11 mM) and CTAB (50 mM). After incubating for 4 µhours at 28° C., AuNR were purified and redispersed in Cetyltrimethylammonium chloride (CTAC, 25 mM). For the silver coating of AuNR, mixing 1 mL AuNR (mean size of 70 nm×30 nm in this example, 12 nM) and 444 µL AgNO$_3$ (10 mM) with 11 mL CTAC (25 mM), followed by the dropwise injection of 444 µL L-ascorbic acid (100 mM). After incubating for 4 hours at 60° C., Au@AgNR were purified, redispersed in CTAB and stored at 4° C. before use.

To assemble the nanoscaled construct, polyT DNA strands were first attached to the nanorods by the thiol-group. The free thiol-DNA was washed away by centrifugation. The polyT DNA strands on the AuNRs or Au@AgNR hybridized with the polyA strands extended from the staple strands of the origami to anchor the AuNRs. The AuNR-DNA and origami were mixed in a range from 5:1 to 20:1 ratio, and annealed from 40° C. to room temperature. The assembled nanoscaled construct may contain dimeric assemblies, i.e. two nanorods joining to one origami structure, or polymeric assemblies, e.g. trimers, or tetramers, or the combination of them. To purify the nanoscaled construct of particular assemblies, the nanoscaled construct was loaded into a 0.7% agarose gel with 11 mM MgCl$_2$. After running the gel electrophoresis at 80 V for 3 hours, the gel band corresponding to the particular fraction of origami-AuNRs, e.g. dimers, could be extracted through an agarose extraction filter.

Examples of controlled assembly ratios of metal nanoparticles on template in order to prepare nanoscaled construct that give a high g-factors (over 10%) or change in g-factors in response to external stimuli are shown in Table 2.

TABLE 2

| | Nanoparticles | | | DNA origami | | Chiral visual response | |
|---|---|---|---|---|---|---|---|
| Materials | Size (length × diameter) | Functionalization molar ratio of thiol-DNA strands: nanoparticles | | Bridge or sensing strands | AuNR-DNA: origami ratio in annealing | g-factor wavelength region | Color example |
| AuNRs | ~70 nm × ~30 nm | 10000:1 | | 1 | 7:1 | 500-800 nm | Blue (Open configuration) |
| AuNRs | ~70 nm × ~30 nm | 10000:1 | | Design1 | 7:1 | 500-800 nm | Red |
| AuNRs | ~70 nm × ~30 nm, ~74 nm × ~33 nm, ~80 nm × ~40 nm | 10000:1 | | Design2.1 | 7:1 | 500-800 nm | Orange |

TABLE 2-continued

| Materials | Nanoparticles | | DNA origami | | Chiral visual response | |
|---|---|---|---|---|---|---|
| | Size (length × diameter) | Functionalization molar ratio of thiol-DNA strands: nanoparticles | Bridge or sensing strands | AuNR-DNA: origami ratio in annealing | g-factor wavelength region | Color example |
| AuNRs | ~70 nm × ~30 nm, ~74 nm × ~33 nm, ~80 nm × ~40 nm | 10000:1 | Design2.2 | 7:1 | 500-800 nm | Yellow (Best range) |
| AuNRs | ~70 nm × ~30 nm, ~74 nm × ~33 nm, ~80 nm × ~40 nm | 10000:1 | Design2.2 without Design2-seq2-14nt | 7:1 | 500-800 nm | Blue (Open configuration) |
| AuNRs (hemispherical end capped) | ~70 nm × ~30 nm | 10000:1 | Design2.2 | 7:1 | 500-800 nm | Orange |
| AuNRs | ~70 nm × ~30 nm, ~74 nm × ~33 nm, ~80 nm × ~40 nm | 10000:1 | Design2.2 | 15:1 | 500-800 nm | Pink |
| AuNRs | ~70 nm × ~30 nm, ~74 nm × ~33 nm, ~80 nm × ~40 nm | 10000:1 | Design2.2 | 20:1 | 500-800 nm | Purple |
| AuNRs | ~70 nm × ~30 nm | 10000:1 | AbsSense | 7:1 | 500-800 nm | Purple; change to red in response to target (antibody) |
| AuNRs | ~70 nm × ~30 nm | 10000:1 | NASense | 7:1 | 500-800 nm | Purple; change to red in response to target (NA) |
| AuNRs | ~70 nm × ~30 nm | 10000:1 | NASense without NASense-sensing strand | 7:1 | 500-800 nm | Orange |
| AuNRs | ~70 nm × ~30 nm | 10000:1 | SMSense | 7:1 | 500-800 nm | Blue; change to purple in response to target (ATP) |
| Au@AgNR-5 nm Ag thickness | ~80 nm × ~40 nm | 40000:1 | / | 7:1 | 400-800 nm | Blue (Open configuration) |
| Au@AgNR-5 nm Ag thickness | ~80 nm × ~40 nm | 40000:1 | Design2.2 | 7:1 | 400-800 nm | Green (Best range) |
| Au@AgNR-8 nm Ag thickness | ~75 nm × ~40 nm | 40000:1 | Design2.2 | 5:1 | 400-800 nm | Pale Green |
| Au@AgNR-5 nm Ag thickness | ~80 nm × ~40 nm | 40000:1 | AbsSense | 5:1 to 10:1 | 400-800 nm | Blue; change to green in response to target (antibody) |
| Au@AgNR-5 nm Ag thickness | ~80 nm × ~40 nm | 40000:1 | NASense | 5:1 to 10:1 | 400-800 nm | Blue; change to green in response to target (NA) |

Key:
AuNRs and Au@AgNRs are cylindrical shaped nanorods unless specified
Design 1 (Design1-seq1, Design1-seq2-21nt),
Design 2.1 (Design2-seq1, Design2-seq2-20nt, Design2-seq3, Design2-seq4),
Design 2.2 (Design2-seq1, Design2-seq2-14nt, Design2-seq3, Design2-seq4)
AbsSense (AbsSense-seq1, AbsSense-seq2)
NASense (NASense-seq1, NASense-seq2, NASense-sensing strand)
SMSense (SMSense-seq1, SMSense-seq2, SMSense-seq3, SMSense-blocker, SMSense-aptamer)

Example 1. Assembly of Nanoscale Construct with g-Factor >10%

To assemble the nanoscaled construct, nanorod functionalization is conducted by polyT DNA strands attached to the nanorods. The attachment can be, for example, by the thiol-modified TTTTT TTTTT TTTTT T (SEQ ID NO:20) DNA strands. The nanorods can be, for example, gold nanorods of size ~70 nm in length and ~30 nm in diameter. The functionalization in the molar ratio between polyT DNA strands and nanorods of 5000:1 to 40000:1. Preferably, the functionalization in the molar ratio between polyT DNA strands and gold nanorods of 10000:1. The functionalization in the molar ratio between polyT DNA strands and silver-coated nanorods of 40000:1. Surfactants are added to the mixture prior to the functionalization method. For example, SDS of final concentration 0.05% is added to the mixture of polyT DNA strands and gold nanorods, SDS of final concentration 0.2% and Tween 20 of final concentration 0.05% are added to the mixture of polyT DNA strands and silver-coated gold nanorods. The functionalization method proposed by Liu et al. (see Liu et al., 2017, for example), is by placing the mixture to a lowering temperature, for example, −20° C. for 2 h. The free unbound DNA was washed away by centrifugation with buffer, for example, 0.5×TBE with 0.1% SDS. The DNA origami (see Kuzyk et al., 2014, for example) and modified with our strands, for example, Design2-seq1, Design1-seq2-14 nt, Design2-seq3, Design2-seq4 in Table 1, are assembled with the functionalized nanorod. The AuNR-DNA and origami were mixed in a range from 5:1 to 20:1 ratio, for example, 7:1 ratio, and annealed from 40° C. to room temperature. The assembled nanoscaled construct, which may contain dimeric assemblies, i.e. two nanorods joining to one origami structure, or polymeric assemblies, e.g. trimers, or tetramers, or the combination of them, as well as unbound nanorods, give the g-factor >10%, for example, 16%.

Example 2. Assembly of Nanoscale Construct with Tunable g-Factor

Geometric configuration of nanoscaled construct can change the g-factor. Geometric configuration of nanoscaled construct can be changed by the presence of the bridge strands, design and length of the bridge stands. Nanoscale construct with open configuration can be made without any modification by bridge strands. Nanoscale construct with close configuration can be made with modification by the bridge strand design 1 (Design1-seq1, Design1-seq2-21 nt), with bridge strand design 2.1 (Design2-seq1, Design1-Design1-seq2-20 nt, Design2-seq3, Design2-seq4), with bridge strand design 2.2 (Design2-seq1, Design1-seq2-14 nt Design2-seq3, Design2-seq4) (FIG. 3a) will give the tunable g-factor ranging from the g-factors 0 to ~16% (FIG. 3b). For example, Nanoscale construct with open configuration gives a g-factor of ~2%, Nanoscale construct with close configuration using design 1 gives a g-factor of ~9%, nanoscale construct with close configuration using design 2.1 gives a g-factor of ~12%, nanoscale construct with close configuration using design 2.2 gives a g-factor of ~16%.

Example buffers for sensing reaction can be 1×TBE or 1×PBS with 5-12 mM $MgCl_2$, optional with 0.02-0.2% sodium dodecyl sulfate (SDS), 0.02-0.2% Tween-20.

Example 3. Protein Sensing with the Nanoscaled Construct

The nanoscaled construct comprises DNA-conjugated digoxigenin (AbsSense in Table 1) that will bind to a protein antibody that interacts with digoxigenin. The angle of our nanoscaled construct changes and hence the chirality upon the interaction between the antibody and the attached digoxigenin in the nanoscaled construct. The change in chirality results in a change in the colorimetric signal from one color to another or the transmission intensity of the polarized light (FIG. 5).

Details on Example 3 of responsivity to external stimuli of antibody detection. The nanoscaled construct incorporated with the bridge strands AbsSense-seq1 and AbsSense-seq2 listed in the Table 1. The nanoscaled construct of concentration in ~1 nM is placed in the sensing reaction buffer 1×PBS with 5 mM $MgCl_2$ and 0.02% SDS. Anti-Digoxigenin antibody of final concentration ~200 μM is added to the nanoscaled construct. The geometric configuration of nanoscaled construct changes. The g-factor changes from the peaks of ~3% to ~9% (FIG. 5b). The color changes from blue to pink when gold nanorods are used in the nanoscaled construct (FIG. 5c). The color changes from blue to green when silver-coated gold nanorods are used in the nanoscaled construct.

Example 4. Nucleic Acid Sensing with the Nanoscaled Construct

The nanoscaled construct comprises specific DNA sequences (NASense in Table 1) that hybridize together, but it is blocked by sensing strand DNA (NASense-sensing strand in Table 1). The presence of cancer genetic marker EGFR (NA in Table 1) will displace the sensing strand DNA from the nanoscaled construct, so the nanoscaled construct will switch from one angle (unhybridized) to another (hybridized); therefore, the chirality will change accordingly. The change in chirality results in a change in the colorimetric signal from one color to another or the transmission intensity of the polarized light (FIG. 6).

Details on Example 4 of responsivity to external stimuli of nucleic acid detection. The nanoscaled construct incorporated with the bridge strands Design1-seq1, NASense-seq1, NASense-seq2 and NASense-sensing strand listed in Table 1. The nanoscaled construct of concentration in ~1 nM is placed in the sensing reaction buffer 1×PBS with 5 mM $MgCl_2$ and 0.02% SDS. Target (NA) of final concentration ~25 nM is added to the nanoscaled construct. The geometric configuration of nanoscaled construct changes. The g-factor change from the peaks of ~3% to ~6% (FIG. 6b). The color changes from blue to pink when gold nanorods are used in the nanoscaled construct (FIG. 6c). The color changes from blue to green when silver-coated gold nanorods are used in the nanoscaled construct.

Example of the responsivity is equivalent to the change in g-factor from 0 to over 10%. Nanoscale construct of DNA origami with open configuration can be made with modification by the bridge strand design 1 (Design2-seq1, Design2-seq3, Design2-seq4) with or without the presence of target nucleic acid (Design1-seq2-14 nt) prior to the assembly with the functionalized nanorod. Without the presence of target nucleic acid in the DNA origami, the g-factor peak can be in the range of 0 to 3%. In the presence of target nucleic acid of final concentration of 500 nM in the DNA origami, the g-factor peak changes to the range of 12 to 16%.

Example 5. Small Molecule Sensing with the Nanoscaled Construct

The nanoscaled construct comprises specific DNA sequences (SMSense in Table 1) that hybridize together, but it is blocked by aptamer and blocker DNA (SMSense-blocker and SMSense-aptamer in Table 1). The presence of small molecule ATP will bind the ATP-binding aptamer from the nanoscaled construct, optionally with the assistant with activating DNA strands (SMSense-activate In Table 1) that lower the kinetic energy required for dissociation of aptamer, so the nanoscaled construct will switch from one angle (unhybridized) to another (hybridized). Therefore, the chirality will change accordingly. The change in chirality results in a change in the colorimetric signal from one color to another or the transmission intensity of the polarized light (FIG. 7).

CITATION LIST

Non Patent Literature

Liu B, et al. J. Am. Chem. Soc. 2017, Vol. 139, No. 28, 9471-9474

Kuzyk A, et al. Nat Mater. 2014, Vol. 13, No. 9, 862-866

The invention claimed is:

1. A nanoscaled construct, said construct comprising or essentially consisting of a nucleic acid structure and at least two separate metallic nanoparticles coupled with said nucleic acid structure,
wherein said at least two separate metallic nanoparticles are at an interchangeable angle to each other,
wherein said at least two separate metallic nanoparticles provide chirality and/or optical activity within the visible and near-infrared (NIR) spectrum from 400 to 800 nm generating a color for the construct,
wherein said construct has an absorption dissymmetry factor (g-factor) of over 10%,
wherein said nucleic acid structure comprises a switchable bridge structure, wherein said angle is adjusted by the open and closed positions of said bridge structure,
wherein the adjustment between the open and closed positions of said switchable bridge structure changes color generation properties of the construct,
wherein the length of said switchable bridge structure affects the color generated by said construct in a closed position of said bridge structure, and
wherein said switchable bridge structure comprises a recognition element, which is specific to a target analyte, and the open and closed positions of said switchable bridge structure are switched due to the presence or absence of said target analyte.

2. The nanoscaled construct according to claim 1, wherein said nucleic acid structure is a DNA origami.

3. The nanoscaled construct according to claim 1, wherein said bridge structure comprises at least two oligonucleotides coupled with said nucleic acid structure, wherein said two oligonucleotides comprise sequences, which are complementary to each other, and wherein the length of the bridge structure affects the color generated by said construct in a closed position of said bridge structure.

4. The nanoscaled construct according to claim 1, wherein the chirality and/or optical activity is reversibly tunable or adjustable.

5. The nanoscaled construct according to claim 1, wherein said metallic nanoparticles are different in size, shape and composition.

6. The nanoscaled construct according to claim 5, wherein the metallic nanoparticles are metallic nanorods.

7. The nanoscaled construct according to claim 5, wherein the metallic nanoparticles are gold nanorods or nanorods composed of gold and silver.

8. The nanoscaled construct according to claim 7, wherein the length of the nanorods is in the range of 60-90 nm and the diameter is in the range of 20-50 nm.

9. The nanoscaled construct according to claim 8, wherein said nanorods are coupled with DNA strands, to said nucleic acid structure, wherein said DNA strands are coupled to said nanorods in a molar ratio of about 10 000:1-40 000:1 to obtain a nanorod-DNA strand assembly, and wherein said DNA strands comprise a sequence which is complementary to the sequence of said nucleic acid structure.

10. The nanoscaled construct according to claim 9, wherein the nanorod-DNA strand assembly is annealed to said nucleic acid structure in molar ratio about 5:1-20:1 in order to obtain polymeric assemblies comprising nanorods coupled with said nucleic acid structure.

11. The nanoscaled construct according to claim 10, wherein dimeric assemblies comprising two nanorods joining one nucleic acid structure are purified from said polymeric assemblies.

12. The nanoscaled construct according to claim 1, wherein the color generation is based on the chiral optical response from metallic nanoparticles.

13. The nanoscaled construct according to claim 1, wherein the color generation is optically detectable by eye and/or optical sensor.

14. The nanoscaled construct according to claim 1, wherein the color is optically detectable with the aid of polarizer or polarizers.

15. The nanoscaled construct according to claim 1, wherein the color can be quantitatively measured by an optical sensor.

16. The nanoscaled construct according to claim 1, wherein a change of the color is based on responsivity to external stimuli.

17. The nanoscaled construct according to claim 16, wherein the responsivity is equivalent to the change in chirality and/or optical activity, or change in g-factor from 0 to over 10%.

18. The nanoscaled construct according to claim 16, wherein the external stimulus is a target analyte.

19. The nanoscaled construct according to claim 16, wherein said nanoscaled construct contains a recognition element as a bioreceptor.

20. A method for detecting an analyte in a sample, the method comprising steps of:
contacting a nanoscaled construct according to claim 1 specific to said analyte with a sample in a test assay, and
detecting said analyte in said sample by optical means or by naked eye,
wherein the presence of the analyte in said sample changes the color of said nanoscaled structure and the change of color in said assay confirms the presence of the analyte in said sample.

21. The method of claim 20, wherein the analyte has a diameter of less than 2 nm.

22. The nanoscaled construct of claim 1, wherein the recognition element is specific to a target analyte having a diameter of less than 2 nm.

* * * * *

SEQUENCE LISTING

```
Sequence total quantity: 20
SEQ ID NO: 1                moltype = DNA   length = 64
FEATURE                     Location/Qualifiers
source                      1..64
                            mol_type = other DNA
                            organism = synthetic construct
SEQUENCE: 1
ataccaaatc gcctatgtta cctttgaatc aagagaaatc aatctccgcc actacactca    60
actc                                                                 64

SEQ ID NO: 2                moltype = DNA   length = 50
FEATURE                     Location/Qualifiers
source                      1..50
                            mol_type = other DNA
                            organism = synthetic construct
SEQUENCE: 2
tgagagttcg taaaacagga agcattaatg agttgagtgt agtggcggag                50

SEQ ID NO: 3                moltype = DNA   length = 70
FEATURE                     Location/Qualifiers
source                      1..70
                            mol_type = other DNA
                            organism = synthetic construct
SEQUENCE: 3
ataccaaatc gcctatgtta cctttgaatc aagagaaatc aatctccgcc actacactca    60
actcaaatac                                                           70

SEQ ID NO: 4                moltype = DNA   length = 36
FEATURE                     Location/Qualifiers
source                      1..36
                            mol_type = other DNA
                            organism = synthetic construct
SEQUENCE: 4
gatgttgctt ggtaatagtt gagtgtagtg gcggag                               36

SEQ ID NO: 5                moltype = DNA   length = 30
FEATURE                     Location/Qualifiers
source                      1..30
                            mol_type = other DNA
                            organism = synthetic construct
SEQUENCE: 5
gatgttgctt ggtaatgtgt agtggcggag                                      30

SEQ ID NO: 6                moltype = DNA   length = 44
FEATURE                     Location/Qualifiers
source                      1..44
                            mol_type = other DNA
                            organism = synthetic construct
SEQUENCE: 6
tgagagttcg taaaacagga agcattaatt taccaagcaa catc                       44

SEQ ID NO: 7                moltype = DNA   length = 35
FEATURE                     Location/Qualifiers
source                      1..35
                            mol_type = other DNA
                            organism = synthetic construct
SEQUENCE: 7
cgtaacaaag ctggctggct gaccttcaag aggac                                35

SEQ ID NO: 8                moltype = DNA   length = 45
FEATURE                     Location/Qualifiers
source                      1..45
                            mol_type = other DNA
                            organism = synthetic construct
SEQUENCE: 8
ataccaaatc gcctatgtta cctttgaatc aagagaaatc aattt                     45

SEQ ID NO: 9                moltype = DNA   length = 31
FEATURE                     Location/Qualifiers
source                      1..31
                            mol_type = other DNA
                            organism = synthetic construct
SEQUENCE: 9
tgagagttcg taaaacagga agcattaatt t                                    31

SEQ ID NO: 10               moltype = DNA   length = 42
FEATURE                     Location/Qualifiers
source                      1..42
```

```
                        mol_type = other DNA
                        organism = synthetic construct
SEQUENCE: 10
attgcccaag acttgtgtgt tgagttgagt gtagtggcgg ag                    42

SEQ ID NO: 11           moltype = DNA   length = 43
FEATURE                 Location/Qualifiers
source                  1..43
                        mol_type = other DNA
                        organism = synthetic construct
SEQUENCE: 11
tgagagttcg taaaacagga agcattaatt cacacaagtc ttg                   43

SEQ ID NO: 12           moltype = DNA   length = 31
FEATURE                 Location/Qualifiers
source                  1..31
                        mol_type = other DNA
                        organism = synthetic construct
SEQUENCE: 12
cacacaagtc ttgggcaatt tgcttcaatg c                                31

SEQ ID NO: 13           moltype = DNA   length = 25
FEATURE                 Location/Qualifiers
source                  1..25
                        mol_type = other DNA
                        organism = synthetic construct
SEQUENCE: 13
gcattgaagc aaattgccca agact                                       25

SEQ ID NO: 14           moltype = DNA   length = 64
FEATURE                 Location/Qualifiers
source                  1..64
                        mol_type = other DNA
                        organism = synthetic construct
SEQUENCE: 14
ataccaaatc gcctatgtta cctttgaatc aagagaaatc aatgaacctc actacagtca 60
actc                                                              64

SEQ ID NO: 15           moltype = DNA   length = 36
FEATURE                 Location/Qualifiers
source                  1..36
                        mol_type = other DNA
                        organism = synthetic construct
SEQUENCE: 15
tcccccaggt cgcgtgagtt gactgtagtg aggttc                           36

SEQ ID NO: 16           moltype = DNA   length = 61
FEATURE                 Location/Qualifiers
source                  1..61
                        mol_type = other DNA
                        organism = synthetic construct
SEQUENCE: 16
tgagagttcg taaaacagga agcattaatt cgcgacctgg gggagtattg cggaggaagg 60
t                                                                 61

SEQ ID NO: 17           moltype = DNA   length = 28
FEATURE                 Location/Qualifiers
source                  1..28
                        mol_type = other DNA
                        organism = synthetic construct
SEQUENCE: 17
gcttcaatgc cacttgtgtc ccccaggt                                    28

SEQ ID NO: 18           moltype = DNA   length = 31
FEATURE                 Location/Qualifiers
source                  1..31
                        mol_type = other DNA
                        organism = synthetic construct
SEQUENCE: 18
cgcgacctgg gggagtattg cggaggaagg t                                31

SEQ ID NO: 19           moltype = DNA   length = 24
FEATURE                 Location/Qualifiers
source                  1..24
                        mol_type = other DNA
                        organism = synthetic construct
SEQUENCE: 19
gggggacaca agtggcattg aagc                                        24
```

```
SEQ ID NO: 20          moltype = DNA   length = 16
FEATURE                Location/Qualifiers
source                 1..16
                       mol_type = other DNA
                       organism = synthetic construct
SEQUENCE: 20
tttttttttt tttttt                                                              16
```